United States Patent [19]

Barthelemy et al.

[11] Patent Number: 5,560,869
[45] Date of Patent: Oct. 1, 1996

[54] STABILIZED COMPOSITIONS COMPRISING 1,1-DICHLORO-1-FLUOROETHANE AND USE OF THESE COMPOSITIONS AS BLOWING AGENTS IN PREMIXES INTENDED FOR THE PREPARATION OF POLYURETHANE FOAMS

[75] Inventors: Pierre Barthelemy, Pietrebais; Annie Leroy, Fauvillers, both of Belgium

[73] Assignee: Solvay (Société Anonyme), Brussels, Belgium

[21] Appl. No.: 364,468

[22] Filed: Dec. 27, 1994

[30] Foreign Application Priority Data

Dec. 27, 1993 [BE] Belgium .................... 09301470

[51] Int. Cl.$^6$ .................................................... C09K 3/00
[52] U.S. Cl. .................................................... 252/372
[58] Field of Search ........................................ 252/372

[56] References Cited

FOREIGN PATENT DOCUMENTS

| | | |
|---|---|---|
| 538085 | 4/1993 | European Pat. Off. . |
| 539719 | 5/1993 | European Pat. Off. . |
| 559264 | 9/1993 | European Pat. Off. . |
| 64-50829 | 2/1989 | Japan . |

OTHER PUBLICATIONS

Polyurethanes 88 Proceedings of the SPI–31st Annual Technical/Marketing Conference, Oct. 18–21, 1988, pp. 73–76, "Accelerated Aging Study of HCFC 141b in Polyurethane Premixes", R. M. Crooker, et al.

CA 120:325393 Nov. 22, 1993.

CA 117:172825 May 7, 1992.

*Primary Examiner*—Paul J. Killos
*Attorney, Agent, or Firm*—Spencer & Frank

[57] ABSTRACT

Stabilized compositions comprising 1,1-dichloro-1-fluoroethane (HFA-141b), a styrene derivative and a co-stabilizing agent chosen from alcohols containing less than 3 hydroxyl groups and non-functionalized alkenes. These compositions may especially be used in premixes for polyurethane foams.

17 Claims, No Drawings

STABILIZED COMPOSITIONS COMPRISING 1,1-DICHLORO-1-FLUOROETHANE AND USE OF THESE COMPOSITIONS AS BLOWING AGENTS IN PREMIXES INTENDED FOR THE PREPARATION OF POLYURETHANE FOAMS

FIELD OF THE INVENTION

The present invention relates to stabilized compositions comprising 1,1-dichloro-1-fluoroethane (HFA-141b).

TECHNOLOGY REVIEW

Fully halogenated chlorofluorocarbons (CFC), which are suspected of having a harmful effect on the ozone layer, may be replaced in a good number of applications (such as, for example, the use as a blowing agent for the preparation of foams, as a solvent, as a heat transfer fluid or as a propellant gas) by fluorohydrocarbons comprising at least one hydrogen atom, which are also referred to as hydrofluoroalkanes (HFA). 1,1-Dichloro- 1-fluoroethane (HFA-141b) is an example of a hydrofluoroalkane which proves to be an advantageous substitute for certain CFCs, especially as an agent for blowing polymer foams and as a solvent.

It is generally recognized that hydrofluoroalkanes must be stabilized in order to avoid any risk of degradation during storage or use. Patent Application EP-A-0,538,085 describes a process for stabilizing HFA-141b using an ethylenic hydrocarbon in particular such as styrene, alpha -methylstyrene and amylene. European Patent Application EP -A-0, 559,264 (SOLVAY) describes a process for the stabilization of a hydrofluoroalkane to counter degradation, according to which from 0.001 to less than 0.1% by weight of an alcohol is added to the said hydrofluoroalkane.

Moreover, HFAs may also be degraded under certain conditions of use. It is for example common practice, in the field of polyurethane foams, to prepare premixes of certain components which are used subsequently for the preparation of the foam. Such premixes usually comprise appropriate amounts of polyol, of blowing agent, of catalyst, of surfactant and of flame retardant. The polyurethane or polyisocyanurate foams may then be prepared by reacting a polyisocyanate with an appropriate amount of such a premix. It has, however, been observed that, in the premixes containing polyols, the hydrofluroalkane used as blowing agent had a tendency to be degraded into various interfering degradation products. These degradation products may have a negative influence on the reactivity of the polyol with the polyisocyanate. Bearing in mind the fact that the storage times of the premixes may be of the order of several months, the reactivity of premixes containing polyols with polyisocyanate will decrease with time, which, from an industrial point of view, is intolerable.

In order to overcome the instability of hydrofluoroalkanes in the presence of compounds containing hydroxyl groups, it is proposed in Japanese Patent Application JP 01/50829 to stabilize them using styrene derivatives. In European Patent Application EP-A-0,539,719, HFA-141b is stabilized using alpha-methylstyrene and/or nitromethane. Nitromethane is preferred and the only example given is of a mixture of nitromethane and alpha-methylstyrene in order to stabilize a premix of HFA-141b and a polyol. Moreover, in the publication Journal of Cellular Plastics, volume 25, 1989, R. M. Crooker et al., pages 609 to 617, it is taught that the addition of alpha-methylstyrene as a stabilizing agent for HFA-141b has no influence on its stability in premixes containing polyols.

It has, however, been observed that, even when alpha-methylstyrene has been added, HFA-141b still undergoes appreciable degradation during storage, especially when it is incorporated in premixes containing polyols.

The aim of the invention is to enhance further the stability of HFA-141b on storage, in particular when it is incorporated in a premix containing a polyol, intended for the manufacture of polyurethane foams.

SUMMARY OF THE INVENTION

The invention consequently relates to compositions comprising 1,1-dichloro-1-fluoroethane and a styrene derivative corresponding to the general formula

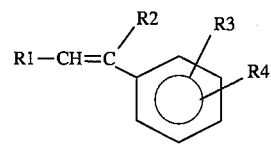

where R1, R2, R3 and R4 independently represent a hydrogen atom or an alkyl group containing from 1 to 3 carbon atoms, characterized in that they comprise a co-stabilizing agent chosen from alcohols containing less than 3 hydroxyl functions and non-functionalized alkenes.

DETAILED DESCRIPTION OF THE INVENTION

The styrene derivatives according to the invention correspond to the general formula

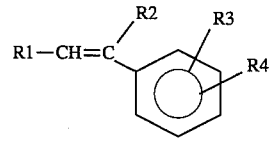

in which R1, R2, R3 and R4 independently represent a hydrogen atom or an alkyl group containing from 1 to 3 carbon atoms. Preferred styrene derivatives are those in which R1, R3 and R4 represent a hydrogen atom. Alpha-methylstyrene is particularly preferred.

The alcohols containing less than 3 hydroxyl functions which may be used in the compositions according to the invention may comprise aliphatic alcohols. When the co-stabilizing agent comprises an aliphatic alcohol, the latter is advantageously a lower alcohol containing from 1 to 3 carbon atoms. Examples of alcohols which may be used according to the invention comprise especially methanol, ethanol, 1-propanol, 2-propanol and ethylene glycol. Methanol is the preferred alcohol.

Among the non-functionalized alkenes which may be used in the compositions according to the invention, acyclic alkenes containing at least 4 carbon atoms are preferred. Advantageously, the alkenes contain not more than 20 carbon atoms. Acyclic alkenes which are especially advantageous are, in particular, branched alkenes. Among the branched alkenes, 2-methyl-2-butene, 2-methyl -1-butene, 3-methyl -1-butene and mixtures thereof are preferred. Very good results have been obtained with industrial 2-methyl-2-butene, usually referred to as amylene, which may contain a small amount of 2-methyl-1-butene.

In the compositions according to the invention, the co-stabilizing agent may consist exclusively of at least one alcohol or of at least one alkene as are defined above.

According to an advantageous variant of the invention, the co-stabilizing agent comprises at least one alcohol and at least one alkene as are defined above.

In the compositions according to the invention, the amount of 1,1-dichloro-1-fluoroethane is generally greater than 85% by weight, preferably greater than 95% by weight. Compositions which contain at least 99% by weight of 1,1-dichloro-1-fluoroethane are particularly preferred.

In the compositions according to the invention, the amount of the styrene derivative is, in general, at least 0.001% by weight relative to the weight of the 1,1-dichloro-1-fluoroethane. The amount of the styrene derivative is preferably at least 0.01%. The amount of the styrene derivative generally does not exceed 10% by weight relative to the weight of the 1,1-dichloro-1-fluoroethane. The amount of the styrene derivative preferably does not exceed 1%.

The compositions according to the invention generally comprise the co-stabilizing agent in an amount at least equal to 0.0001% by weight relative to the weight of the 1,1-dichloro-1-fluoroethane. Preferably, they comprise the co-stabilizing agent in an amount by weight at least equal to 0.001%. The amount of co-stabilizing agent generally does not exceed 10% by weight relative to the weight of the 1,1-dichloro-1-fluoroethane. The amount by weight of co-stabilizing agent preferably does not exceed 1% relative to the weight of the 1,1-dichloro-1-fluoroethane.

In the particular case in which the co-stabilizing agent comprises an alcohol as defined above, the alcohol is advantageously in an amount by weight which does not exceed 0.1% of the weight of the 1,1-dichloro-1-fluoroethane.

The compositions according to the invention may consist essentially of 1,1-dichloro-1-fluoroethane, styrene derivative and co-stabilizing agent. As a variant, they may contain additional additives, the choice and quantities of which will depend on the use for which the compositions are intended.

The compositions according to the invention may be used as cleaning agents, for example as solvents for degreasing metal articles. They may also be used as heat transfer fluids in refrigeration equipment or as propellant gases for aerosol products. The compositions according to the invention may be used advantageously as blowing agents for the preparation of polymer foams, in particular polyurethane or polyisocyanurate foams.

Consequently, the invention also relates to the use of the compositions according to the invention as blowing agents for preparing polymer foams, in particular polyurethane or polyisocyanurate foams.

The invention also relates to premixes intended for the preparation of polyurethane or polyisocyanurate foams, comprising a polyol and a blowing agent, the blowing agent comprising a composition in accordance with the invention, as defined above.

In the premixes according to the invention, the polyol is not critical and may be any polyol commonly used for the manufacture of polyurethane or polyisocyanurate foams. Examples of polyols which may be used in the premixes according to the invention are polyol polyethers and polyol polyesters. The optimum proportion of blowing agent relative to the polyol in the premixes will depend on various parameters, especially the type of foam to be prepared and the nature of the polyol. It may be readily determined in each particular case. In practice, in the premixes according to the invention, from 1 to 50 parts by weight of the composition according to the invention are generally used per 100 parts by weight of polyol.

The premixes according to the invention may consist only of the polyol and of the composition according to the invention. As a variant, they may contain one or more other blowing agents. As a general rule, they often comprise surfactants, catalysts, flame retardants and possibly other additives which are usually used for preparing polyurethane foams.

The premixes according to the invention have proven to be particularly stable on storage. They are suitable for the manufacture of rigid polyurethane foams.

The invention also relates to polyurethane or polyisocyanurate foams obtained by the use of a composition in accordance with the invention or of a premix in accordance with the invention, as are defined above.

EXAMPLES

The examples which follow serve to illustrate the invention, among these examples, Examples 1R, 2R and 3R are reference examples, which are not in accordance with the invention. Examples 4, 5 and 6 are in accordance with the invention.

Example 1R (Reference)

A premix for the manufacture of a polyurethane foam was prepared by mixing (amounts by weight):

- 70 parts of polyol IXOL®B251 (SOLVAY),
- 130 parts of CARADOL®585-8 aminopolyol based on sucrose (SHELL),
- 50 parts of trichloropropyl phosphate,
- 2 parts of TEGOSTAB®B1048 silicone-containing surfactant (GOLDSCHMIDT),
- 2 parts of water
- 48 parts of blowing agent consisting of 1,1-dichloro-1-fluoroethane (HFA-141b) and 0.1% by weight of alpha-methylstyrene relative to the weight of the HFA-141b,
- 2.4 parts of N,N-dimethylethanolamine,
- 1.6 parts of potassium acetate KACEKAT®KCA (SOLVAY FLUOR UND DERIVATE).

Two successive measurements were made in order to estimate the stability of the premix on storage.

Firstly, immediately after its preparation, half of this premix was mixed with 147.7 parts of methylenebis(4-phenyl isocyanate) MDI®44V20 (BAYER) and the reactivity profile of this premix was characterized by measuring 5 characteristic parameters of the polyurethane foam thus obtained: the cream time, the string time, the rise time, the tack-free time and the curing time. These times are defined as the times measured starting from the beginning of the agitation of the mixture until the following:

- cream time: until the time when a colour change of the mixture is observed and which corresponds to when the foam begins to rise;
- string time: until the time when the formation of polymer strings is observed after a glass stick has been contacted with the foam,
- rise time: until the time when the full rise of the foam is achieved;
- tack-free time: until the time when the surface tackiness of the foam disappears;
- curing time: until the time when a stiff shape is obtained.

The other half of the premix was stored at 50° C. in the presence of a mild steel test piece. After storage for 30 days at 50° C., this matured premix was mixed with 147.7 parts of methylene bis(4-phenyl isocyanate) MDI®44V20 and the reactivity profile of this premix was characterized by measuring the 5 parameters mentioned above.

The stability of the premix is estimated by the variation of the abovementioned parameters during storage, the premix being proportionally more stable the smaller this variation.

The results are found in Table I.

Example 2R (Reference)

An identical premix to the premix of Example 1R was prepared, except that the blowing agent consisted of a mixture of 1,1-dichloro-1-fluoroethane (HFA-141b) and 0.1% by weight of amylene relative to the weight of the HFA-141b.

The stability of the premix was evaluated as in Example 1R, by comparing its reactivity profile after storage for 30 days, at 50° C. and in the presence of a mild steel test piece, with its initial reactivity profile. The results are found in Table I.

Example 3R (Reference)

An identical premix to the premix of Example 1R was prepared, except that the blowing agent consisted of a mixture of 1,1-dichloro-1-fluoroethane (HFA-141b) and 0.01% by weight of methanol relative to the weight of the HFA-141b.

The stability of the premix was evaluated as in Example 1R, by comparing its reactivity profile after storage for 30 days, at 50° C. and in the presence of a mild steel test piece, with its initial reactivity profile. The results are found in Table I.

Example 4 (In Accordance with the Invention)

An identical premix to the premix of Example 1R was prepared, except that a composition in accordance with the invention was used for the blowing agent, this composition comprising 1,1-dichloro-1-fluoroethane (HFA-141b), 0.05% by weight of alpha-methylstyrene and 0.05% by weight of amylene relative to the weight of the HFA-141b.

The stability of the premix was evaluated as in Example 1R, by comparing its reactivity profile after storage for 30 days, at 50° C. and in the presence of a mild steel test piece, with its initial reactivity profile. The results are found in Table I.

Example 5 (In Accordance with the Invention)

An identical premix to the premix of Example 1R was prepared, except that a composition in accordance with the invention was used for the blowing agent, this composition comprising 1,1-dichloro-1-fluoroethane (HFA-141b), 0.1% by weight of alpha-methylstyrene and 0.01% by weight of methanol relative to the weight of the HFA-141b.

The stability of the premix was evaluated as in Example 1R, by comparing its reactivity profile after storage for 30 days, at 50° C. and in the presence of a mild steel test piece, with its initial reactivity profile. The results are found in Table I.

Example 6 (In Accordance with the Invention)

An identical premix to the premix of Example 1R was prepared, except that a composition in accordance with the invention was used for the blowing agent, this composition comprising 1,1-dichloro-1-fluoroethane (HFA-141b), 0.1% by weight of alpha-methylstyrene, 0.005% by weight of amylene and 0.01% by weight of methanol relative to the weight of the HFA-141b.

The stability of the premix was evaluated as in Example 1R, by comparing its reactivity profile after storage for 30 days, at 50° C. and in the presence of a mild steel test piece, with its initial reactivity profile. The results are found in Table I.

TABLE I

| | | Examples | | | | | |
|---|---|---|---|---|---|---|---|
| | | 1R | 2R | 3R | 4 | 5 | 6 |
| cream T | initial | 22 | 25 | 25 | 24 | 23 | 24 |
| (s) | after 30 days | 32 | 31 | 34 | 32 | 30 | 27 |
| | variation (%)* | 45 | 24 | 36 | 33 | 30 | 13 |
| string T | initial | 66 | 71 | 68 | 70 | 68 | 65 |
| (s) | after 30 days | 98 | 97 | 100 | 98 | 92 | 77 |
| | variation (%) | 48 | 37 | 47 | 40 | 35 | 18 |
| tack-free T | initial | 98 | 102 | 105 | 110 | 102 | 98 |
| (s) | after 30 days | 150 | 150 | 165 | 150 | 140 | 112 |
| | variation (%) | 53 | 47 | 57 | 36 | 37 | 14 |
| rise T | initial | 110 | 110 | 110 | 110 | 110 | 110 |
| (s) | after 30 days | 140 | 140 | 150 | 140 | 130 | 135 |
| | variation (%) | 27 | 27 | 36 | 27 | 18 | 23 |
| curing T | initial | 4 | 4 | 4 | 4.5 | 4 | 4 |
| (min) | after 30 days | 6.5 | 6.5 | 7 | 6.5 | 6 | 5 |
| | variation (%) | 63 | 63 | 75 | 44 | 50 | 25 |

*variation = [(T after 30 days - T initial)/T initial] × 100

The results in this table show that the premixes in accordance with the invention, in Examples 4, 5 and 6, are more stable on storage than the premixes of the Comparative Examples 1R, 2R and 3R. These results are particularly visible as regards the tack-free time and the curing time.

What is claimed is:

1. A composition comprising 1,1-dichloro-1-fluoroethane and a styrene derivative corresponding to the general formula

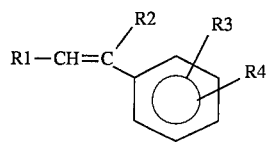

where R1, R2, R3 and R4 independently represent a hydrogen atom or an alkyl group containing from 1 to 3 carbon atoms, said compositions comprising in addition a co-stabilizing agent chosen from alcohols containing less than 3 hydroxyl functions and non-functionalized alkenes.

2. A composition according to claim 1, wherein the co-stabilizing agent comprises at least one alcohol containing less than 3 hydroxyl functions and at least one non-functionalized alkene.

3. A composition according to claim 1, wherein the styrene derivative is selected from those in which R1, R3 and R4 represent a hydrogen atom.

4. A composition according to claim 3, wherein the styrene derivative is alpha-methylstyrene.

5. A composition according to claim 1 wherein the amount of styrene derivative is from 0.01 to 1% by weight relative to the weight of the 1,1-dichloro-1-fluoroethane.

6. A composition according to claim 1 wherein, when the co-stabilizing agent comprises an alcohol, said alcohol is an aliphatic alcohol containing from 1 to 3 carbon atoms.

7. A composition according to claim 6, wherein the alcohol is methanol.

8. A composition according to claim 1 wherein, when the co-stabilizing agent comprises an alkene, said alkene is selected from 2-methyl-2-butene, 2-methyl-1-butene, 3-methyl-1-butene and mixtures thereof.

9. A composition according to claim 1 comprising the co-stabilizing agent in an amount by weight of from 0.0001 to 10% relative to the weight of the 1,1-dichloro-1-fluoroethane.

10. A composition according to claim 9 comprising the co-stabilizing agent in an amount by weight of from 0.001 to 1% relative to the weight of the 1,1-dichloro-1-fluoroethane.

11. A composition according to claim 10 wherein, in the case where the co-stabilizing agent comprises an alcohol, the amount by weight of alcohol does not exceed 0.1% relative to the weight of the 1,1-dichloro-1-fluoroethane.

12. In a blowing agent for the preparation of polymer foams, the improvement comprising a composition according to claim 1.

13. In a polyurethane or polyisocyanurate foam, the improvement comprising a blowing agent comprising a composition according to claim 1.

14. In a premix for preparing polyurethane or polyisocyanurate foam comprising a polyol and a blowing agent, the improvement comprising said blowing agent comprising a composition in accordance with claim 1.

15. A polyurethane or polyisocyanurate foam prepared with a blowing agent comprising a composition according to claim 1.

16. A polyurethane or polyisocyanurate foam prepared with a premix according to claim 14.

17. A composition comprising 1,1-dichloro-1-fluoroethane and alpha-methylstyrene, said composition comprising in addition a co-stabilizing agent consisting essentially of either an aliphatic alcohol containing from 1 to 3 carbon atoms present in an amount by weight not exceeding 0.1% relative to the weight of the 1,1-dichloro-1-fluoroethane, or an alkene selected from the group consisting of 2-methyl-2-butene, 2-methyl-1-butene, 3-methyl-1-butene, and mixtures thereof.

* * * * *